United States Patent

Murakami et al.

[11] Patent Number: 5,914,089
[45] Date of Patent: Jun. 22, 1999

[54] METHOD OF STERILIZATION AND DISINFECTION BY OZONE

[75] Inventors: Atsushi Murakami, Shimizu; Yukio Akahori, Fujieda; Akiyoshi Okamoto, Shizuoka, all of Japan

[73] Assignee: Masao Suzuki, Shizuoka, Japan

[21] Appl. No.: 08/634,581

[22] Filed: Apr. 18, 1996

[51] Int. Cl.$^6$ .............................. A01N 2/08; A01N 25/02; C02F 1/78
[52] U.S. Cl. ............................ 422/28; 210/760; 424/405; 424/613
[58] Field of Search ............................... 422/28, 105, 292, 422/108; 210/760; 261/DIG. 42; 424/405, 613

[56] References Cited

U.S. PATENT DOCUMENTS

| | | |
|---|---|---|
| 4,827,727 | 5/1989 | Caracciolo . |
| 5,053,140 | 10/1991 | Hurst ...................................... 422/28 X |
| 5,443,801 | 8/1995 | Langford .................................. 422/294 |

FOREIGN PATENT DOCUMENTS

| | | |
|---|---|---|
| 2-7967 | 1/1990 | Japan . |
| 6-233805 | 8/1994 | Japan . |
| 7-108056 | 4/1995 | Japan . |

Primary Examiner—Elizabeth McKane
Attorney, Agent, or Firm—Wenderoth, Lind & Ponack, L.L.P.

[57] ABSTRACT

Hereby established is a method of disinfection by ozone which is safe, clean, more reliable, and more efficient than prior methods. The method comprises a step of calculating the amount of ozone which would be required to solely disinfect bacteria if there were no co-existing materials, a step of calculating the amount of ozone which will be consumed by actual co-existing materials and a step of applying the total value of the two ozone amounts in proper forms, such as, gas or liquid, etc., preferably in the form of aqueous solution, to the object to be disinfected. This method can be consistently adopted for disinfection on very wide varieties of bacteria.

10 Claims, No Drawings

METHOD OF STERILIZATION AND DISINFECTION BY OZONE

BACKGROUND OF THE INVENTION

1. Field of the Invention

This invention relates to a method for sterilizing and disinfecting skin or apparatuses easily, quickly, safely, consistently, and efficiently by using ozone.

2. Description of the Related Art

Many types of chemicals have been conventionally used for sterilization and disinfection, and nowadays many types of chemicals are used practically. However, none of these currently used germicides and disinfectants can be definitely effective on all bacteria and viruses. In addition, different concentrations and exposure times specific to each chemical are required to exhibit the sterilization effect. Therefore, in case of an emergency, it is difficult to have enough time for complete sterilization and disinfection. Some chemicals involve safety problems such as skin allergy or corrosion of apparatus, and some chemicals involve problems of leaving residues and requiring post-treatment steps. As described herein above, all commercially available disinfectants are disadvantageous specifically individually in consistency, quick remedy, and safety, so improved disinfectants are required.

Ozone has been known as a substance having a strong sterilizing effect for many years. However, ozone is a vapor and inconvenient for handling, and in the event of inhalation of high concentration ozone, it exhibits strong toxicity depending on the condition. Therefore, the use of ozone has been suspended historically. For finger disinfection, which is essential for preventing in-hospital infection, ozone washing in which an ozone aqueous solution is used is convenient, but the solubility of ozone in water is low and the concentration of ozone is difficult to be controlled. Therefore, investigators have obtained different results when studying the relationship between ozone concentration in an aqueous solution and its sterilizing effect. For this reason, conditions for use of ozone washing have not been established, and manuals have not been issued. Increasing ozone concentration to intensify the sterilizing power permits an easy sterilization and disinfection. However, vapor ozone vaporizing from the solution increases, thereby causing a problem in safety. These reasons have delayed the practical use of ozone for sterilization and disinfection.

Nevertheless, ozone is very effective for sterilizing and disinfecting a wide variety of bacteria, and ozone is remarkably superior to other germicides and disinfectants in its strong sterilizing and disinfecting power due to its active oxidation action. Accordingly, such sterilizing and disinfecting power of ozone is very advantageous. The vapor phase feature favors ozone to be used for vapor phase sterilization and disinfection of the inside of a room and apparatuses, and the reduced residual property and easy post-treatment steps provide safety advantages.

Therefore, it is would be an important improvement in the prevention of in-hospital infection and public health if the strong sterilizing and disinfecting effect of an ozone aqueous solution and ozone gas could be used safely and consistently.

The present invention is intended to solve the above mentioned problems, by providing a method of safe and consistent sterilization and disinfection by calculating the amount of ozone required for the sterilization, thereby contributing to the prevention of in-hospital infection and improvement of public health.

SUMMARY OF THE INVENTION

In order to solve the above-mentioned problems, the present invention provides a method of sterilization and disinfection using ozone, wherein ozone in an amount, which is more than the total of the amount required to sterilize and the amount consumed by materials co-existing with bacteria, is applied to the object, whereby complete sterilization is accomplished safely without impact of the above mentioned co-existing materials.

In detail, the reason of the above mentioned fault of inconsistent results from conventional investigations on evaluation of sterilizing and disinfecting power of ozone is attributed to the design of the experiments, which experiments lack consideration of the fact that ozone solubility in water is as low as ppm, unlike the cases of other germicides and disinfectants. Since ozone is an extremely reactive substance, ozone oxidizes very easily oxidizable substances in co-existing materials including a culture medium for bacteria. Accordingly, ozone is rapidly consumed. Since the amount of ozone dissolved in water is inherently trace, and the trace amount of ozone is consumed for oxidation of co-existing materials, the amount of ozone is insufficient for sterilization, namely the original purpose of ozone. In view of the usual commercially available disinfectants which contain an effective component on the order of a % rather than ppm, the serious impact of the competitive reaction at such low concentration specific to ozone has not been recognized. In quantitative experiments for evaluation of the sterilizing and disinfecting power, although the concentration is considered, the concept of quantity has not been taken into consideration. Thus conventional investigations on ozone sterilization have overlooked this simple mistake.

It is required to create the equation for calculating an initial concentration of ozone and quantity of ozone aqueous solution required for sterilization and disinfection by paying attention to the time based consumption of ozone keeping the quantity of co-existing materials and bacteria in mind or in other words, the rate equation of the competitive reaction. To calculate the rate equation of these competitive reactions, the impact of as many various related factors must be clarified, including the impact of bacterial types. This is the feature of the present invention.

In vitro experiments on ozone aqueous solution sterilization and disinfection have led to the simple conclusions described herein under.

1) Sterilization by ozone is completed in a moment, and ozone consumption is synchronous with sterilization.
2) Amount of ozone required for sterilization rarely depends on bacterial type.
3) Amount of ozone required to sterilize one bacterium is 40 attograms ($4 \times 10^{-17}$ gram).
4) The total ozone amount is the determinative factor, and the initial ozone concentration to the solution and the amount of solvent are not determinative.
5) Reducing co-existing materials consume ozone quickly, and compete with sterilization of bacteria.
6) Various co-existing substances involved in surgical operations such as blood and pus are ozone consuming substances.
7) Ozone consumption background to be consumed by co-existing materials is measurable prior to sterilization.

As described herein above, it is not necessary to calculate the required amount of ozone based on complex equations with time. Instead, the above mentioned conclusions lead to a simple conclusion that necessary and sufficient amount of ozone should be used and the impact of factors other than the above mentioned are negligible. In other words, an insufficient amount of ozone as compared with the sufficient amount as mentioned above causes insufficient sterilization and residual bacteria.

The necessary and sufficient amount of ozone is calculated easily as described herein under. Approximate values and standard deviation values of the amount of bacteria and oxidizable co-existing materials in a sample are determined prior to sterilization. It is convenient to represent the ozone amount by a product of usual ppm concentration and the amount of aqueous solvent.

a) Calculation of sterilization ozone amount (A) based on an estimated amount of bacteria in an sample.
b) Calculation of the amount of ozone consumption (B) based on a co-existing material amount in a sample.
c) Calculation of total necessary ozone amount (T) by summing ozone amounts (A) and (B).
d) Calculation of the amount of ozone solution (V) by dividing the total amount of necessary ozone (T) by ozone concentration (C).

Otherwise, (C) is calculated by dividing (T) by (V). Ozone solution concentration (C) of 4 ppm or lower is easy to use for usual sterilization and disinfection since the vaporization of ozone into the atmosphere is slight. Therefore, safety in the operation environment is high. However, a high concentration ozone solution may be used in special cases.

If a large amount of oxidizable co-existing materials exist, it is recommended that the co-existing materials be removed by pre-washing and then sterilization and disinfection be carried out according to the procedure b) and the following. The solution used for pre-washing is completely disinfected using a high concentration ozone solution or suitable methods.

Practically, the ozone amount added is calculated in terms of safety factor, so that the resultant sterilization will be perfect even for any unexpected situation. Hazardous excessive use of ozone is suppressed, and further post-treatment is very easy because of the unstable property and the trace amount specific to ozone. Therefore, discharge from facilities does not cause environmental pollution.

The above-mentioned conclusion is a fundamental principle of ozone sterilization. Further, the invention is not limited to aqueous sterilization. The invention is applied also to vapor phase sterilization. In this case, the reactive and easily decomposable nature of ozone vapor is advantageous in preventing pollution while the residual property of ethyleneoxide in conventional gas sterilization is disadvantageous. The present invention realizes consistent sterilization with high reproducibility by using proper amount of ozone, and provides a method of safe sterilization at low cost.

The method of sterilization and disinfection by ozone of the present invention provides perfect sterilizing and disinfecting effect by applying the above mentioned principle. Details of the invention will be described hereinafter.

To sterilize bacteria found in hospitals, the amount of ozone required to sterilize bacteria and the amount of ozone consumed by co-existing materials are added to secure the total ozone amount for sterilization. 4 ppm ozone aqueous solution within a treatment time of as short as 5 seconds is enough for complete sterilization with no residual bacteria. This capability of perfect sterilization within such a short time is true for only ozone and not for any other conventional germicides. Furthermore, ozone sterilizes perfectly drug-resistant bacteria, such as MRSA as well as non-variants, which causes many in-hospital infections.

By utilizing this highly-effective sterilizing method, hand sterilization is possible in a short time. By washing the hands in 4 ppm ozone aqueous solution for 30 seconds, a perfect sterilization of the hand with no residual bacteria is achieved. Conventionally, the hand sterilization required washing the hands for 10 minutes or longer using commercially available conventional disinfectants. Thus, it is easily understood that hand sterilization in accordance with the present invention is much better, and is an important technique necessary for emergency operation.

The method of the present invention is also applied to sterilize medical apparatus and garments. Perfect prevention of bacterial infection is possible within a short time. Ozone gas is suitable for sterilization of the inside of a room and furniture. Furthermore, ozone gas is excellent in post-treatment and residual property as compared with formalin fumigation and ethyleneoxide sterilization, and the short time requirement is definitely advantageous over other conventional methods.

According to this method of sterilization and disinfection, perfect sterilization and disinfection is possible by using proper ozone concentration and amount and paying attention to various conditions specific to the case, such as skin or apparatus, in-door or out-door, and good or bad ventilation. One of the features of this method is its flexibility to various cases. Since residual ozone amount in discharge is very small in accordance with the present invention, post-treatment is very easy and the method will not cause environmental pollution.

By applying the proper ozone amount and concentration of ozone in accordance to the condition of the subject to be sterilized, perfect sterilization can be carried out safely, consistently, and simply.

DESCRIPTION OF THE PREFERRED EMBODIMENT

It is confirmed by experiments described hereinafter that the method of sterilization and disinfection by ozone in accordance with the present invention exhibits perfect sterilizing and disinfecting effect by applying the above mentioned principle. For the convenience of quantitative determination, liquid phase reaction was selected and ozone aqueous solution was used for experiments.

EXAMPLE 1

Sterilizing Effect on Bacteria in Hospitals (in vitro experiment)

Eight bacteria of *Escherichia coli, Pseudomonas aeruginosa, Bacillus subtilis, Staphylo coccusaureus, Klebsiella pneumoniae, Proteus mirabilis, Serratia marcescens* and *Candida albicans*, which are generally found in a hospital, were selected to carry out in vitro experiments using ozone aqueous solution. A certain amount of a bacteria suspension which contained $10^5$ and $10^8$ bacteria in 1 ml suspension was added to 10 times volume of 4 ppm ozone aqueous solution. After 5, 10, 30, and 60 seconds, a certain amount of stopping solution was added thereto to decompose excessive ozone to stop the sterilization at that time. These solutions were transferred to a flat medium respectively, cultured for 24 hours at a prescribed temperature, and then the number of colonies was counted. As a result of this experiment, it was confirmed that sterilization by ozone solution for 5 seconds is enough for the death of all types of bacteria and for all number of bacteria described herein above. This experiment was an example of a case involving the safe factor. In the case when the ozone amount was not more than the calculated value, the sterilization was incomplete. For example, when 9 times volume of 3.5 ppm ozone aqueous solution was added to a certain amount of bacteria suspension which contained $10^{12}$ bacteria in the same manner as the previous experiment described herein above, it was confirmed that, for all types of bacteria, the number of bacteria decreased only to $10^2$ order after 5 seconds, and remained at that value for 3 minutes after that. Thus, from this experiment, the present invention was verified.

EXAMPLE 2

Sterilizing Effect on MRSA (in vitro Experiment)

MRSA is a variant of yellow staphylococcus and is resistant to antibiotics. MRSA is considered a principal cause of in-hospital infection, and is a target of in-hospital disinfection. These bacteria are categorized as the coagulase type and classified into seven types from 1 to 7, each type having different resistance patterns to antibiotics. It is the purpose of this experiment to clarify whether the resistance of these types to ozone is different or not, although resistance of these types to chemical drugs are different. Suspensions containing all types of MRSA bacteria totalling $10^9$ and $10^{12}$ in 1 ml of suspension were used and tested in the same manner as described in Example 1. Un-varied yellow staphylococcus (MRSA) was used as reference under the same condition. The result showed that the amount of residual bacteria was zero when sterilizing the bacteria for 5 seconds in all cases regardless of the types of variants. No difference was found between the variants and un-varied MRSA. Therefore, the sterilization by ozone aqueous solution is also effective against antibiotic resistant variants.

EXAMPLE 3

Washing Hand Sterilization and Disinfection

Surgical personnel wash their hands to sterilize the bacteria on their hands before beginning the operation. The process of sterilization is carried out by putting a sterilized surgical glove on one hand and pouring 50 ml of sterilized physiological salt solution into the glove. By rubbing the fingers from the outside, the bacteria on the hand are removed into the solution even when the bacteria are located in difficult places such as finger forks, foot of nails, and palm prints. This sterilization method is referred to as the glove juice method. The bacteria in the glove solution were then counted by the flat medium method described in Example 1, and the obtained value was prescribed as background value of hand bacteria. The other hand was washed carefully using a brush and ozone aqueous solution. The number of bacteria in the washed solution was counted by the flat medium method. After washing, the number of residual bacteria on the hand was counted by glove juice method in the same manner as described for background value. The experimental result found that the sterilization washing using 4 ppm ozone aqueous solution for 30 seconds was enough for perfect sterilization. The background bacteria value ranged from several hundred to several thousand depending on individuals and conditions of the hand. However, there were no cases in which the number was nearly zero. In cases where the hand was dirty with fat, blood or pus, it was required to prewash using a small amount of surfactant. Under a condition of sterilization using 4 ppm ozone aqueous solution for 30 seconds, no incompatibility and irritation to skin was found. As a result, washing time can be shortened from conventional 10 minutes or more to only 30 seconds.

EXAMPLE 4

Sterilization and Disinfection of Medical Apparatus

Medical apparatuses such as forceps, scalpels and tweezers can also be sterilized by ozone aqueous solution. A bacterial suspension which contained $10^8$ bacteria was applied on the apparatus after use. The apparatus was then put into a beaker, sterilized by stirring for 1 minute in ozone aqueous solution, and transferred into a sterilized physiological salt solution with sterilized tweezers to be washed. The number of residual bacteria was then counted by the flat medium method. The result confirmed complete sterilization with no presence of residual bacteria. In cases where the apparatus is very dirty with, for example, blood, pre-washing with surfactant is effective.

EXAMPLE 5

Sterilization and Disinfection of Medical Garments

A piece of cloth about 5 cm by 5 cm was sampled from a medical garment. A bacteria suspension which contained $10^8$ bacteria was then applied to the sample. The sample was dried and then placed in a beaker. 50 ml of 4 ppm ozone aqueous solution was then added thereto, followed by gentle stirring for 2 minutes. The sample was then taken out using a sterilized tweezer, and the number of residual bacteria was counted in the same manner as described in Example 4. The result confirmed perfect sterilization with no residual bacteria.

As described hereinbefore, the method of sterilization and disinfection by ozone according to the present invention employs the total amount of ozone as calculated by adding the ozone amount required to sterilize bacteria and the ozone amount consumed by co-existing materials, so that complete sterilization of bacteria is accomplished in a short period of time without affecting the co-existing materials. This method is extremely effective in preventing in-hospital infection which in turn, solve the major problems concerning drug resistant bacteria and improve public health. Further, since the total amount of the ozone is calculated so as to keep the ozone concentration as small as possible, the safety in sterilization and disinfection can be improved, resulting in a small possibility of environmental pollution.

What is claimed is:

1. A method for disinfecting a hand using ozone, comprising:
    a) calculating a sterilization ozone amount (A) based on an estimated amount of bacteria in a sample and based on a rate of 40 attograms or higher of ozone per bacterium;
    b) calculating a consumption ozone amount (B) based on an amount of materials co-existing with said bacteria in said sample;
    c) adding together said amount (A) and said amount (B) to calculate a total ozone amount (T);
    d) producing ozone water having a predetermined ozone concentration (C), wherein said ozone concentration (C) is 4 ppm or lower ozone in water;
    e) calculating a necessary volume (V) of ozone water by dividing said total ozone amount (T) by said ozone concentration (C) and
    f) applying substantially as much as said volume (V) of said ozone water to said hand to be disinfected for a time of 30 seconds or less.

2. The method according to claim 1, further comprising a step of pre-washing said hand using a surfactant prior to said steps a)–f).

3. A method for disinfection of an object using ozone water comprising:
   a) calculating a sterilization ozone amount (A) based on an estimated amount of bacteria in a sample and based on a rate of 40 attograms or higher of ozone per bacterium;
   b) calculating a consumption ozone amount (B) based on an amount of materials co-existing with said bacteria in said sample;
   c) adding together said amount (A) and said amount (B) to calculate a total ozone amount (T);
   d) producing ozone water having a predetermined ozone concentration (C);
   e) calculating a necessary volume (V) of ozone water by dividing said total ozone amount (T) by said ozone concentration (C);
   f) applying substantially as much as said volume (V) of said ozone water to the object to be disinfected.

4. The method according to claim 3, wherein said object to be disinfected is a solid object.

5. The method according to claim 4, wherein said solid object is a medical apparatus, a medical garment or a glove.

6. The method according to claim 5, further comprising a step of pre-washing said solid object using a surfactant prior to said steps a)–f).

7. The method according to claim 4, wherein said solid object is human skin or a human hand, and wherein said concentration (C) is 4 ppm or lower ozone in water, and wherein the contact time of said human skin or human hand with said ozone water is 30 seconds or less.

8. The method according to claim 7, further comprising a step of pre-washing said human skin or human hand using a surfactant prior to said steps a)–f).

9. The method according to claim 4, further comprising a step of pre-washing said solid object using a surfactant prior to said steps a)–f).

10. The method according to claim 3, further comprising a step of pre-washing said object using a surfactant prior to said steps a)–f).

* * * * *